United States Patent [19]
Wilson et al.

[11] B 3,982,034
[45] Sept. 21, 1976

[54] FLAVORING WITH 2,4,6-TRIMETHYL-S-TRITHIANE

[75] Inventors: Richard Arnold Wilson, Edison; Ira Katz, Elberon; Manfred H. Vock, Locust, all of N.J.; Edward J. Shuster, Brooklyn, N.Y.

[73] Assignee: International Flavors & Fragrances Inc., New York, N.Y.

[22] Filed: Mar. 21, 1975

[21] Appl. No.: 560,717

[44] Published under the second Trial Voluntary Protest Program on February 10, 1976 as document No. B 560,717.

Related U.S. Application Data

[62] Division of Ser. No. 166,683, July 28, 1971, abandoned.

[52] U.S. Cl.................................. 426/535; 252/522
[51] Int. Cl.²................... A23L 1/231; A23L 1/235; A23L 1/226
[58] Field of Search .................... 260/243 R, 327 T; 426/535

[56] References Cited
UNITED STATES PATENTS

| | | | |
|---|---|---|---|
| 2,213,804 | 9/1940 | Lincoln et al. | 260/327 UX |
| 2,594,379 | 4/1952 | Barch | 426/533 |

OTHER PUBLICATIONS

Chem. Abstracts, Vol. 44, 1950, 16952c, Abstracting Food Research, pp. 15322–15325, (1950).

Pippen et al., Hydrogen Sulfide, A Direct and Potentially Indirect Contributor to Cooked Chicken Aroma, J. Food Science, 34, 1969, pp. 443–446.

*Primary Examiner*—Joseph M. Golian
*Attorney, Agent, or Firm*—Arthur L. Liberman; Harold Haidt

[57] ABSTRACT

A small but effective amount of a compound represented by the formula

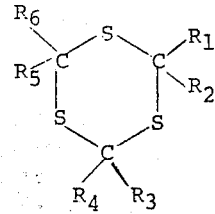

wherein $R_1$, $R_3$, and $R_5$ are the same and are lower alkyl of from 1 to 5 carbon atoms and $R_2$, $R_4$, and $R_6$ are the same and are hydrogen or lower alkyl of from 1 to 5 carbon atoms, is used to alter the flavor and aroma characteristics of a consumable material.

1 Claim, No Drawings

FLAVORING WITH 2,4,6-TRIMETHYL-S-TRITHIANE

This application is a divisional application of Ser. No. 166,683, filed July 28, 1971 and now abandoned.

This invention has to do with the use of certain trithianes and dithiazines to alter the flavor and aroma of consumable materials.

The term "consumable material" includes foodstuffs, perfumed materials (e.g. perfumes, colognes, soaps and aftershave lotions) and tobacco.

The term "foodstuff" as used herein includes both solid and liquid ingestible materials for man or animals, which materials usually do, but need not, have nutritional value. Thus, foodstuffs include meats, gravies, soups, convenience foods, malt and other alcoholic or non-alcoholic beverages, nut butters such as peanut butter and other spreads, seafoods including fish, crustaceans, mollusks and the like, candies, breakfast foods, baked goods, vegetables, cereals, soft drinks, snack foods, pet foods such as dog and cat foods, other veterinary products, and the like.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like, as well as tobacco substitutes intended to replace natural tobacco, such as lettuce and cabbage leaves and the like. The tobaccos and tobacco products include those designed or used for smoking such as in cigarette, cigar, and pipe tobacco, as well as products such as snuff, chewing tobacco, and the like.

The term "alter" (in its application to foodstufffs and tobacco) in its various forms will be understood herein to mean the supplying or imparting of a flavor character or note to an otherwise bland, relatively tasteless substance, or augmenting an existing flavor characteristic where the natural flavor is deficient in some regard, or supplementing the existing flavor impression to modify the organoleptic character.

There is a continuing search for compositions which can vary, fortify, modify, enhance or otherwise improve (i.e. "alter") the flavor and aroma of a foodstuff. To be fully satisfactory, such compositions should be stable, non-toxic, and blendable with other ingredients to provide their own unique flavor and aroma nuance without detracting from the co-ingredients. Preferably, such compositions should be naturally occurring or present in natural foodstuffs (although unrecognized as flavor components thereof) so that their ingestible safety can be readily recognized. Additionally, these materials should be capable of being synthesized in a simple and economic manner.

Various heterocyclic poly-S- compounds have been shown in the literature to have flavor implications. For example, in U.S. Pat. No. 3,503,758 to Wada et al, pentathiepane, tetrathiane and tetrathiepane are said to have a flavor and aroma; and Chang in *Chemistry and Industry*, 1639, Nov. 23, 1968, reports 3,5-dimethyl-1,2,4-trithiolune as present in the volatiles of boiled beef. Other investigators have commented that poly alkyl trithianes are odorless or have an intensely putrid odor. See Barch, U.S. Pat. No. 2,594,379 and Breslav and Skolnik, "Heterocyclic Compounds", p. 726, *Interscience* (1966). Pippen in *Journal of Food Science*, 34, p. 443–446 (1969) speculated that $H_2S$ reacted with a carbonyl compound in chicken fat and postulated that 2,4,6-trimethyl-S-trithiane could be one of the products formed.

It has now been found that the flavor of a foodstuff can be altered by adding thereto a small but effective amount of at least one heterocyclic poly —S— compound having the formula

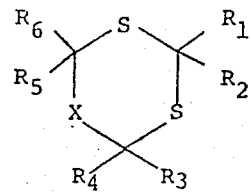

wherein X is S or $-NR_7-$; and (1) when X is S, then $R_1$, $R_3$, and $R_5$ are the same and are lower alkyl of from 1 to 5 carbon atoms and $R_2$, $R_4$, and $R_6$ are the same and are hydrogen or lower alkyl from 1 to 5 carbon atoms; or (2) when X is $-NR_7-$, then $R_1$, $R_3$, and $R_5$ are the same and are lower alkyl of from 1 to 5 carbon atoms, $R_2$, $R_4$, and $R_6$ are hydrogen, and $R_7$ is hydrogen or lower alkyl of from 1 to 5 carbon atoms. The invention also contemplates flavoring compositions containing such heterocyclic poly —S— compounds.

A particularly preferred class of such compounds includes the dithiazines of the formula

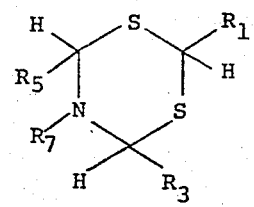

wherein $R_1$, $R_3$ and $R_5$ are the same lower alkyl radical of 1 to 5 carbon atoms and $R_7$ is hydrogen or a lower alkyl radical of 1 to 5 carbon atoms. Suitable dithiazines include:
2,4,6-trimethyldihydro-1,3,5-dithiazine
2,4,5,6-tetramethyldihydro-1,3,5-dithiazine
2,4,6-tri-isopropydihydro-1,3,5-dithiazine
2,4,6-tri-n-butyldihydro-1,3,5,-dithiazine
2,4,6-tri-isobutyldihydro-1,3,5-dithiazine
2,4,6-tri-n-pentyldihydro-1,3,5-dithiazine
and mixtures thereof. The dithiazines have a pleasant sweet cereal, nutty taste and are especially suitable for beef, meat, nut and burnt flavors.

Another class of preferred heterocyclic poly-S-compounds include the trithianes having the formula

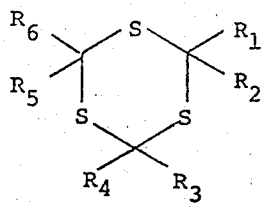

wherein $R_1$, $R_3$, and $R_5$ are the same and are lower alkyl of from 1 to 5 carbon atoms and $R_2$, $R_4$, and $R_6$ are the same and are hydrogen or lower alkyl from 1 to 5 carbon atoms. Suitable trithianes are:

2,4,6-trimethyl-s-trithiane
2,2,4,4,6,6,-hexamethyl-s-trithiane
2,4,6-triethyl-s-trithiane
2,4,6-triethyl-2,4,6-trimethyl-s-trithiane
2,4,6-tri-t-butyl-s-trithiane
2,4,6-tri-n-butyl-s-trithiane
2,4,6-tri-isopropyl-s-trithiane
2,4,6-tri-n-propyl-s-trithiane
2,2,4,4,6,6,-hexaethyl-s-trithiane
2,2,4,4,6,6-hexaisopropyl-s-trithiane
2,4,6-triethyl-2,4,6-tri-n-pentyl-s-trithiane The trithianes have a sweet nutty aroma and taste and are suitable for fruit (gooseberry, black currant, grape, raspberry) nut and meat flavors.

The structural formulae given herein contemplate and include cis- and trans- and other conformational isomers.

The dithiazines are prepared by using convention processes, such as the methods shown in Beilstein, 27, pp. 460–462 and 2d *Suppl.*, p. 524. The trithianes are similarly known compounds and can be prepared in a known manner such as that described by Campaigne, *Chem. Reviews*, 39, No. 1, pp. 1–77, August 1946. Applicants have also found that the compounds: 2,4,6-trimethyldihydro-1,3,5-dithiazine; 2,4,6-trimethyl-s-trithiane; and 2,2,4,4,6,6-hexamethyl-s-trithiane, are present in the volatiles of beef extract.

Such heterocyclic-poly-S- compounds are useful in flavoring compositions and to alter the flavor of foodstuffs. They are especially adapted for adding sweet, meaty and nut nuances to consumable materials and in rounding out and improving the character and quality of meat flavors.

When the heterocyclic poly-S- compounds according to this invention are used in a flavoring composition, they can be combined with conventional flavoring materials or adjuvants. Such co-ingredients or flavoring adjuvants are well known in the art for such use and have been extensively described in the literature. Apart from the requirement that any such adjuvant material be ingestibly acceptable, and thus non-toxic or otherwise non-deleterious, conventional materials can be used and broadly include other flavor materials, vehicles, stabilizers, thickeners, surface active agents, conditioners and flavor intensifiers.

Such conventional flavoring materials include saturated and unsaturated fatty and amino acids, alcohols, including primary and secondary alcohols; esters, carbonyl compounds including ketones and aldehydes; lactones, other cyclic organic materials including benzene derivatives, alicyclics, heterocyclics such as furans, pyridines, pyrazines and the like; sulfur-containing materials including thiols, sulfides, disulfides and the like; proteins; lipids; carbohydrates; so-called flavor potentiators such as monosodium glutamate, guanylates, and inosinates; natural flavoring materials such as cocoa, vanilla and caramel; essential oils and extracts such as anise oil, clove oil and the like; artificial flavoring materials such as vanillin; and the like. Particularly useful flavoring agents and adjuncts are cyclopentane thiol, protein hydrolysate, such as hydrolyzed vegetable protein, cysteine, salts of cysteine such as cysteine hydrochloride, thiamine, salts of thiamine, 2,5-dimethyl-3-hydroxy-4-oxo-4,5-dihydrofuran, and products resulting from heating a mixture of at least two differing materials of the foregoing and high pressure reaction products of $H_2S$ and 2,5-dimethyl-3-hydroxy-4-oxo-4,5-dihydrofuran.

Stabilizers include preservatives such as sodium chloride, and the like; antioxidants such as calcium and sodium ascorbate, ascorbic acid, butylated hydroxyanisole, butylated hydroxytoluene, propyl gallate and the like; sequestrants such as citric acid, EDTA, phosphates, and the like.

Thickeners include carriers, binders, protective colloids, suspending agents, emulsifiers and the like, such as agar-agar, carrageenan, cellulose and cellulose derivatives such as carboxymethyl cellulose and methyl cellulose, natural and synthetic gums such as gum arabic, gum tragacanth and the like, and other proteinaceous materials; lipids, carbohydrates, starches and pectins.

Surface active agents include emulsifying agents such as mono- and/or diglycerides of fatty acids such as caproic acid, caprylic acid, palmitic acid, myristic acid, oleic acid, and the like; lecithin; defoaming and flavor-dispersing agents such as sorbitan monostearate, potassium stearate, hydrogenated tallow alcohol, and the like.

Conditioners include compounds such as bleaching and maturing agents such as benzoyl peroxide, calcium peroxide, hydrogen peroxide and the like; starch modifiers such as peracetic acid, sodium chlorite, sodium hypochlorite, propylene oxide, succinic anhydride and the like; buffers and neutralizing agents such as sodium acetate, sodium diacid phosphate, ammonium bicarbonate, ammonium phosphate, citric acid, lactic acid, vinegar and the like; colorants such as carminic acid, cochineal, turmeric, curcumin, approved food and drug dyes, and the like; firming agents such as aluminum sodium sulfate, calcium chloride and calcium gluconate; texturizers; anti-caking agents such as aluminum calcium sulfate and tribasic calcium phosphate; enzymes, yeast foods such as calcium lactate and calcium sulfate; nutrient supplements such as iron salts, such as ferric phosphate, ferric pyrophosphate, ferrous gluconate and the like, riboflavin, vitamins; zinc sources such as zinc chloride, zinc sulfate, and the like.

The heterocyclic-poly-S-compounds, or the compositions incorporating them, as mentioned above, can be combined with one or more vehicles or carriers for adding them to the particular product. Vehicles can be edible or otherwise suitable materials such as ethyl alcohol, propylene glycol, water, and the like. Carriers include materials such as gum arabic, carrageenan, other gums, and the like. The heterocyclic-poly-S-compounds can be incorporated with the carriers by conventional means such as spray-drying, drum drying, and the like. Such carriers can also include materials for coacervating the heterocyclic-poly-S- compounds (and other flavoring ingredients, as present) to provide encapsulated products. When the carrier is an emulsion, the flavoring composition can also contain emulsifiers such as mono- and diglycerides of fatty acids and the like. With these carriers or vehicles, the desired physical form of the composition can be prepared.

It will be understood by those skilled in the art that the heterocyclic-poly-S- compounds can be added to the materials to be flavored at any convenient point in the production of the finished product. Thus, when they are used to alter or otherwise vary the flavor of a foodstuff, they can be added in the original mixture, dough, emulsion, batter, or the like, prior to any cooking or heating operation. Alternatively, they can be added at a later stage of processing if volatilization losses would be excessive during the earlier processing.

When the materials are used to treat tobacco products, for example, the additive can be applied in a suitable manner by spraying, dipping or otherwise. The heterocyclic-poly-S-compounds can be applied during the "casing" or final spray treatment of the tobacco, or they can be applied at some earlier stage of curing. The quantity of heterocyclic-poly-S- compounds or mixtures thereof utilized should be sufficient to impart the desired flavor characteristic to the product, but on the other hand, the use of an excessive amount of the heterocyclic-poly-S- compounds is not only wasteful and uneconomical but in some instances too large a quantity may unbalance the flavor or other organoleptic property of the product to be consumed. The quantity used will vary depending upon the ultimate foodstuff, tobacco product, or other consumable product; the amount and type of flavor initially present in the product; the further process or treatment steps to which the product will be subjected; regional and other preference factors; the type of storage, if any, to which the product will be subjected; and the preconsumption treatment, such as baking, frying, and so on, given to the product by the ultimate consumer.

It is accordingly preferred that the ultimate compositions contain from about 0.02 parts per million (ppm) to about 100 ppm of the heterocyclic-poly-S- compounds. More particularly, in food compositions it is desirable to use from about 0.02 to about 20 ppm and in certain preferred embodiments of the invention, from about 0.1 to about 15 ppm of the heterocyclic-poly-S- compounds are included in the finished product. On the other hand, tobacco compositions can contain as little as 0.02 ppm and as much as 100 ppm, depending upon whether a cigarette tobacco, a pipe tobacco, a cigar tobacco, a chewing tobacco, or snuff is being prepared.

All parts, proportions, percentages, and ratios herein are by weight unless otherwise indicated.

The amount of heterocyclic-poly-S- compounds to be utilized in flavoring or flavor-enhancing compositions can be varied over a wide range depending upon a particular quality to be added to the foodstuff, tobacco, or other consumable material. Thus, amounts of one or more heterocyclic-poly-S- compounds according to the present invention from about 0.1 up to 80 or 90% can be incorporated in such compositions. It is generally found to be desirable to include from about 0.5 to about 25% of the heterocyclic-poly-S-compounds in such compositions.

The heterocyclic poly-S-compounds of this invention can also be added to perfume compositions in their pure form or they can be added to mixtures of materials in fragrance-imparting compositions to provide a desired fragrance character to a finished perfume material. The perfume and fragrance compositions obtained according to this invention are suitable in a wide variety of perfumed articles and can also be used to improve, enhance, modify, alter or reinforce fragrance materials. It will thus be appreciated that the heterocyclic poly-S-compounds and mixtures thereof of this invention are useful as olfactory agents and fragrances.

The term "perfume composition" is used herein to mean a mixture of compounds, including for example, natural oils, synthetic oils, alcohols, aldehydes, ketones, esters, lactones, and frequently hydrocarbons which are admixed so that the combined odors of the individual components produce a pleasant or desired fragrance. Such perfume compositions usually contain: (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials. Such perfume compositions or the novel materials of this invention can be used in conjunction with carriers, vehicles, solvents, dispersants, emulsifiers, surface-active agents, aerosol propellants, and the like. In perfume compositions, the individual components contribute their particular olfactory characteristics, but the overall effect of the perfume composition will usually at least be the sum of the effect of each ingredient. Thus, the heterocyclic poly-S-compounds of this invention can be used to alter the aroma characteristics of a perfume composition, for example, by highlighting or moderating the olfactory reaction contributed by another ingredient of the composition.

The amount of one or more compounds of this invention which will be effective in perfume compositions depends on many factors, including the other ingredients, their amounts and the effects which are desired. It has been found that perfume compositions containing as little as 1.0% by weight of the compounds of this invention, or even less can be used to intensify or augment and enhance various types of fragrance compounds, the odors of which may be desired to be imparted to colognes, perfumes, bath oils and other cosmetic products. The amount employed will depend on considerations of cost, nature of the end product, the effect desired in the finished product, and the particular fragrance sought. Higher concentrations (e.g. 2% by weight) of the heterocyclic-poly-S-compounds of this invention will intensify the green leafy note and green nutty notes of the compositions.

The heterocyclic poly-S-compounds disclosed herein can be used in a composition as an olfactory component of a fragrance which in turn can be used in perfumes, colognes, bath preparations (such as bath oils and bath salts) and the like. When the heterocyclic poly-S-compounds of this invention are used in finished perfumed articles, such as the foregoing, they can be used in amounts of 0.04% by weight or lower.

The following examples are given to illustrate embodiments of the invention as it is presently preferred to practice it. It will be understood that these examples are illustrative, and the invention is not to be considered as restricted thereto except as indicated in the appended claims.

EXAMPLE I

The following materials are homogeneously mixed at 25°C:

| INGREDIENTS | PARTS |
| --- | --- |
| Vegetable shortening | 622.7 |
| Salt | 321.7 |
| Glutamic acid | 5.1 |
| L-cysteine hydrochloride | 10.3 |
| Glycine | 5.1 |
| β-Alanine | 1.3 |
| Taurine | 20.0 |
| Mixture of di-sodium inosinate and di-sodium guanylate | 3.3 |

The mixture is heated at 300°F for thirty seconds. After cooling to 100°F, 0.12 part of diacetyl and 0.10 part of hexanal are added. After aging the resulting mixture for three hours, 0.1 part of 2,4,6-trimethyl-dihydro-1,3,5-dithiazine is added.

The resulting mixture is aged for ten hours to provide a material having an excellent chicken aroma.

EXAMPLE II

| INGREDIENTS | PARTS |
| --- | --- |
| Vegetable shortening | 622.7 |
| Salt | 321.7 |
| Glutamic acid | 5.1 |
| L-Cysteine hydrochloride | 10.3 |
| β-Alanine | 1.3 |
| Taurine | 20.0 |
| Mixture of di-sodium inosinate and di-sodium guanylate | 3.3 |
| 2,4,6-trimethyl-s-trithiane | 0.1 |

The mixture is heated to 300°F for thirty seconds. After cooling to 100°F, 0.12 part of diacetyl and 0.10 part of hexanal are added.

The resulting mixture has an excellent chicken aroma.

EXAMPLE III

The following ingredients are homogeneously mixed at 25°C:

| INGREDIENTS | PARTS |
| --- | --- |
| Vegetable shortening | 622.7 |
| Salt | 321.7 |
| Glutamic Acid | 5.1 |
| L-Cysteine hydrochloride | 10.3 |
| Glycine | 5.1 |
| β-Alanine | 1.3 |
| Taurine | 20.0 |
| Mixture of di-sodium inosinate and di-sodium guanylate | 3.3 |

The mixture is heated to 300°F for thirty seconds. After cooling to 100°F, 0.12 part of diacetyl, 0.10 part of hexanal, and 0.1 part of 2, 4, 5, 6-tetramethyl-dihydro-1, 3, 5-dithiazine are added.

The resulting mixture has an excellent chicken aroma.

EXAMPLE IV

The following ingredients are homogeneously mixed at 25° C:

| INGREDIENTS | PARTS |
| --- | --- |
| Vegetable shortening | 622.7 |
| Salt | 321.7 |
| Glutamic acid | 5.1 |
| L-Cysteine hydrochloride | 10.3 |
| Glycine | 5.1 |
| β-Alanine | 1.3 |
| Taurine | 20.0 |
| Mixture of di-sodium inosinate and di-sodium guanylate | 2.0 |

The mixture is heated to 300°F for sixty seconds. After cooling to 100°F, 0.12 part of diacetyl and 0.10 part of hexanal are added. After aging the mixture for a period of three hours at a temperature of 65°F, 0.1 part of 2,4,6-triethyl-2,4,6-tri-n-pentyl-s-trithiane are added. The resulting mixture is then aged for ten hours to yield a composition having an excellent chicken aroma and flavor.

EXAMPLE V

Cysteine hydrochloride in the amount of 8.8 g is refluxed at 215°F under atmospheric pressure for four hours with a mixture of 309 g of hydrolyzed vegetable protein and 674 g of water. Subsequent to the reflux, the mixture is cooled and 0.05 g of 2,4,6-trimethyldihydro-1,3,5-dithiazine is added and intimately admixed with the composition. The mixture has an excellent beef flavor.

EXAMPLE VI

Cyclopentane thiol and 2,2,4,4,6,6-hexamethyl-s-trithiane (1:1 mole ratio) in the amount of 0.05 g. are refluxed at 215°F under atmospheric pressure for four hours with the following premix composition:

| Ingredients | Amount |
| --- | --- |
| Hydrolyzed vegetable protein (Maggi 4BE) | 309 g |
| Water | 674 g |
| Thiamine-HCl | 8.8 g |
| Cysteine-HCl | 8.8 g |

Subsequent to the reflux period, the resulting mixture is aged for 72 hours at 60°–75°C. The mixture has an excellent beef aroma.

EXAMPLE VII 2,4,6-Trimethyl-s-trithiane in the amountn of 0.05 g is refluxed at 215°F under atmospheric pressure for four hours with the following pre-mix composition:

| INGREDIENTS | AMOUNT |
| --- | --- |
| Hydrolyzed vegetable protein (Maggi 4BE) | 309 g |
| Cysteine-HCl | 8.8 g |
| Thiamine-HCl | 8.8 g |
| Water | 674 g |

Subsequent to the reflux, the resulting mixture is aged for 72 hours at 60°–75°C. The mixture has an excellent beef aroma.

EXAMPLE VIII

The composition prepared in Example I is dissolved in propylene glycol to provide a 0.1% solution. This solution in the amount of 0.966 g is added to 7.3 g of a soup base consisting of:

| INGREDIENTS | PARTS |
| --- | --- |
| Fine ground sodium chloride | 35.62 |
| Hydrolyzed vegetable protein | 27.40 |
| Monosodium glutamate | 17.81 |
| Sucrose | 10.96 |
| Beef fat | 5.48 |
| Sethness caramel color (powder B&C) | 2.73 |

The resulting mixture is added to 12 ounces of boiling water to obtain a soup having an excellent chicken flavor.

The composition of Example VI (0.005 g) when added to the above soup base also provides a soup having good meat flavor.

EXAMPLE IX

The composition prepared in Example V is dissolved in propylene glycol to provide a 0.1% solution. This solution in the amount of 0.966 g is added to 7.3 g of a soup base consisting of:

| INGREDIENTS | PARTS |
| --- | --- |
| Fine ground sodium chloride | 35.62 |
| Hydrolyzed vegetable protein (Maggi 4BE) | 27.40 |
| Monosodium glutamate | 17.81 |
| Sucrose | 10.96 |
| Beef fat | 5.48 |
| Caramel color, bakers and confectioner's powder grade | 2.73 |

The resulting mixture is added to 12 ounces of boiling water to obtain a soup having an excellent chicken flavor.

The composition of Example II (0.005 g) when added to the above soup base also provides a soup having good meat flavor.

EXAMPLE X

One-half gram of the soup base mixture of Example VIII is emulsified in a solution containing 100 g gum arabic and 300 g water. The emulsion is spray-dried with a Bowen Lab Model Drier utilizing 250 cfm of air with an inlet temperature of 500°F, an outlet temperature of 200°F, and a wheel speed of 50,000 rpm.

Twelve grams of the spray-dried material is mixed with 29.2 g of the soup base set forth in Example VIII. The resulting mixture is then added to 12 ounces of boiling water and an excellent meat flavored soup is obtained.

EXAMPLE XI

Example I is repeated except that the dithiazine is replaced by 0.003 part of a mixture comprising the following ingredients:

| INGREDIENTS | PARTS |
| --- | --- |
| 2,4,6-trimethyl dihydro-1,3,5-dithiazine | 10 |
| 2,4,6-trimethyl-s-trithiane | 26 |
| Corn Oil | 50 |
| Gum arabic | 20 |

The resulting mixture has an excellent meat flavor

EXAMPLE XII

Preparation of Perfume Composition Containing 2,4,6-Trimethyl-S-Trithiane

The following composition is prepared:

| INGREDIENTS | PARTS BY WEIGHT |
| --- | --- |
| 2,4,6-trimethyl-s-trithiane | 4 |
| Benzyl butyrate | 4 |
| Bois de Rose | 10 |
| Citronellyl formate | 30 |
| Citronellyl acetate | 20 |
| Geraneol coeur | 200 |
| Citronellol coeur | 300 |
| Menthone | 5 |
| Menthol natural | 5 |
| Rose oxide | 10 |
| Geranyl acetate | 30 |
| Dimethyl Benzylcarbinylacetate | 2 |
| | 620 |

The addition of the 2,4,6-trimethyl-s-trithiane in the quantity given imparts a green leafy note similar to that of natural geranium Bourbon to the composition without detracting from the quality of the odor.

EXAMPLE XIII

The following formulations are produced:

Formulation A
| | |
| --- | --- |
| 1.9 gm | Natural black currant juice, concentrate |
| 0.1 gm | Natural black currant esters |
| 10.0 ml | Sugar Syrup 32°Be |
| q.s. 100 ml | Spring water |

Formulation B
| | |
| --- | --- |
| 1.9 gm | Natural black currant juice, concentrate |
| 0.1 gm | Buchu leaf oil 0.1% (ethanol 95%) |
| 10.0 ml | Sugar Syrup 32°Be |
| q.s. 100 ml | Spring water |

Formulation C
| | |
| --- | --- |
| 1.9 gm | Natural black currant juice, concentrate |
| 0.1 gm | Niribine* 10% (ethanol 95%) |
| 10.0 ml | Sugar Syrup 32°Be |
| q.s. 100 ml | Spring water |

*Niribine is produced by distilling an alcoholic macerate of black currant buds.

Formulation D
| | |
| --- | --- |
| 1.9 gm | Natural black currant juice, concentrate |
| 0.1 gm | 2,4,6-trimethyl-s-trithiane 0.1% (ethanol 95%) |
| 10.0 ml | Sugar Syrup 32°Be |
| q.s. 100 ml | Spring water |

Formulation E
| | |
| --- | --- |
| 1.9 gm | Natural black currant juice, concentrate |
| 0.1 gm | 2,4,6-trimethyl-s-trithiane 0.01% (ethanol 95%) |
| 10.0 ml | Sugar Syrup 32°Be |
| q.s. 100 ml | Spring Water |

Formulation F
| | |
| --- | --- |
| 1.9 gm | Natural black currant juice, concentrate |
| 10.0 ml | Sugar Syrup 32°Be |
| q.s. 100 ml | Spring water |

Each of the above-mentioned formulations is compared with one another by a panel composed of 10 tasters. Formulation F is generally considered by the panel to be flat and not very characteristic for fresh black currant. Formulations B, C, D and E are considered as having substantially fresh and more pleasant notes than formulation F. In summary, formulations D and E were preferred as the best black currant juice formulations. In conclusion, for use in black currant flavor, the material 2,4,6-trimethyl-s-trithiane can be used at rates of one-tenth of that of Buchu leaf oil in black currant juice.

It is further to be concluded that 2,4,6-trimethyl-s-trithiane can successfully replace Buchu leaf oil, Niribine and/or natural black currant esters wherever the ingredient is used in reinforced black currant juices, substituted black currant juices and imitation black currant flavors.

We claim:

1. A process for altering, modifying or enhancing the black currant flavor of a foodstuff having a black currant taste which comprises adding thereto from about 0.02 up to 100 parts per million by weight of a substantially pure form of 2,4,6-trimethyl-S-trithiane.

* * * * *